United States Patent [19]

Cox et al.

[11] Patent Number: 5,034,189

[45] Date of Patent: Jul. 23, 1991

[54] FLUORESCENT PROBE FOR RAPID MEASUREMENT OF ANALYTE CONCENTRATION

[75] Inventors: Mary E. Cox, Flushing, Mich.; Jennifer W. Parker, Los Angeles, Calif.

[73] Assignee: The Regents of the University of California, Alameda, Calif.

[21] Appl. No.: 769,881

[22] Filed: Aug. 27, 1985

[51] Int. Cl.$^5$ .............................. G01N 33/00
[52] U.S. Cl. ...................... 422/52; 422/681; 422/55; 422/56; 422/57; 422/58; 422/52; 422/60; 435/817; 436/95; 436/172; 436/163
[58] Field of Search ............ 436/95, 172, 163; 422/68, 55-60; 435/817

[56] References Cited

U.S. PATENT DOCUMENTS

| RE 31,879 | 5/1985 | Lubbers | 422/58 |
|---|---|---|---|
| 3,873,267 | 3/1975 | Swartz | 422/90 |
| 4,003,707 | 1/1977 | Lübbers et al. | 436/68 |
| 4,221,567 | 9/1980 | Clark et al. | 436/68 |
| 4,321,057 | 3/1982 | Buckles | 422/58 |
| 4,436,094 | 3/1984 | Cerami | 436/95 |
| 4,476,870 | 10/1984 | Peterson et al. | 128/634 |
| 4,525,265 | 6/1985 | Abe et al. | 204/415 |
| 4,568,518 | 2/1986 | Wolfbeis et al. | 436/172 |

OTHER PUBLICATIONS

Cox et al., Applied Optics, vol. 24(14), Jul. 15, 1985.
CA 76:39547c, Johnson et al.
CA 74:69921w, Tolstorozhev et al.
Bowen et al., J of Phy. Chem., 1959 (63), pp. 4–7.

*Primary Examiner*—Robert J. Warden
*Assistant Examiner*—Timothy M. McMahon
*Attorney, Agent, or Firm*—Poms, Smith, Lande & Rose

[57] ABSTRACT

A fluorescent optical probe employed for the analysis of the concentration of an analyte (or material to be analyzed) in a fluid, employs a permeable, transparent polymeric matrix in which a fluorophor is immobilized, with the polymeric material being directly exposed to the fluid being analyzed. The composite material of the probe may be made up of a homogeneous matrix of transparent polymer, fluorescent compound, catalyst(s) and reagents(s) and is employed to measure analyte concentration in a fluid in the environment surrounding the material. For analyzing oxygen, the fluorophor may be 9,10-diphenyl anthracene and the polymer matrix may be poly (dimethyl siloxane), or silicone, with the presence of oxygen quenching the fluorescence of 9,10-diphenyl anthracene. For analyzing the concentration of glucose, the polymeric material may be poly (hydroxyethyl methacrylate), or PHEMA, the fluorophor may be 9,10-diphenyl anthracene, and as catalytic material, glucose oxidase may also be immobilized within the PHEMA matrix to reduce the quenching action of the oxygen, with increased output radiation therefore indicating higher levels of glucose. More generally, the fluorophor, and the catalyst, and other reagents, when utilized, are immobilized, either physically or chemically, in a homogeneous manner throughout the polymer host. Examples of other analytes and catalysts are given.

1 Claim, 7 Drawing Sheets

FIG. 1

A = ANALYTE
C = CATALYST
Q = QUENCHER
F,=
F*= } FLUOR. MAT; EXCITED-*

FIG. 3

9,10-DIPHENYL ANTHRACENE
SOLVENT PDMS
CONCENTRATION $3 \times 10^{-4}$ M
TEMPERATURE (°C)
○ 2.0
□ 10.0
△ 25.0
◇ 40.0
▽ 48.0

PARTIAL PRESSURE OF OXYGEN ⟶
(MOLAR % OF OXYGEN)

*THE RECIPROCAL OF THE ABSOLUTE FLUORESCENCE INTENSITY NORMALIZED TO UNITY AT OXYGEN PARTIAL PRESSURE OF ZERO.

FLUORESCENT PROBE FOR RAPID MEASUREMENT OF ANALYTE CONCENTRATION

FIELD OF THE INVENTION

This invention relates to systems using solid materials containing fluorescent compounds as probes to analyze for the concentration of chemical substances in fluids.

BACKGROUND OF THE INVENTION

It has previously been proposed to measure the concentration of certain analytes (chemical substances being analyzed) such as oxygen ($O_2$) or nitric oxide (NO), by the quenching of fluorescence. Such a technique is an indirect measurement since the gas is not measured per se. Instead, the effect of the gas on fluorescence intensity is measured. Several devices have been proposed to use fluorescence quenching to measure oxygen. In such devices, radiation is applied through a fiber optic element or bundle at the proper radiation frequency to excite the fluorophor. A detector is provided for determining the intensity of the radiation from the fluorophor, which is at a different frequency from the incident radiation. In the presence of oxygen, the radiation from the fluorophor is "quenched" or reduced, so that the intensity of the output radiation from the fluorophor is a function of the concentration of oxygen that is present in the environment surrounding the probe.

Several patents have disclosed this type of system, and three of these patents are D. W. Lubbers U.S. Pat. No. 4,306,877, granted Dec. 22, 1981, Richard G. Buckles U.S. Pat. No. 4,321,057, granted Mar. 23, 1982, and J. I. Peterson, et al. U.S. Pat. No. 4,476,870, granted Oct. 16, 1984. Additional articles which provide some background in this field include an article entitled "Chemical Sensors Based on Fiber Optics", by W. Rudolph Seitz, at pp. 16, 18, 20, 22, 24, 33 and 34, *Analytic Chemistry*, Volume 56, No. 1, January 1984; and an article entitled "Fiber-Optic Sensors for Biomedical Applications", by J. I. Peterson, et al. pp. 123–127, *Science*, Apr. 13, 1984, Volume 224, No. 4645. A number of texts are known which disclose sources for energizing fluorescent material, and detectors for picking up the radiation. These texts which discuss the overall type of system to which the present probes are applicable, include *Principles of Optics* by Max Born and Emil Wolf, Pergamon Press, New York, Third Edition, 1965; *Physical Optics* by R. W. Wood, Dover Publishing Company, 1967; *Radiation and Optics* by John Stone, McGraw-Hill, 1963; and *Optics* by M. V. Klein, John Wiley & Sons, 1970.

The patent to R. G. Buckles, U.S. Pat. No. 4,321,057, purports to disclose structures for measuring the concentration of oxygen by variations in the output fluorescent intensity from a fluorophor; and also that the concentration of glucose may be measured through the effect of a catalyst glucose oxidase on the quenching action of oxygen in reducing the output radiation from a fluorophor. However, the fluorescent analysis structures disclosed in the Buckles patent, for example, include sheaths, of two or more layers of material, and this is typical of the fluorescent analysis devices which have been proposed heretofore. As a result of the use of several layers or sheaths, or membranes, the response times would be relatively long, normally taking in the order of several minutes or more, before equilibrium and a relatively stable output is obtained.

Accordingly, an important object of the present invention is to decrease the response time of analyzing apparatus employing fluorescent material to measure analytes.

Additional objects of the present invention are to provide ease of fabrication at reduced cost; greater flexibility of design of analyte detection system, thereby allowing increased optimization for a given application; and for many applications, superior reliability.

SUMMARY OF THE INVENTION

In general, the present invention involves analysis systems using homogeneous, solid, composite materials containing fluorescent material, wherein the fluorescent material is affected by the concentration of the analytes in the fluid to be analyzed, and the fluorescent radiation intensity is thereby varied.

In accordance with important aspects of the present invention, the probe is formed of a matrix of transparent polymeric material which is permeable to the analyte, and which has the fluorophor and any other essential materials (e.g., catalysts and reagents) immobilized within the matrix of the polymeric material; and the polymeric matrix is directly exposed to the fluid being analyzed. The term "analyte" will frequently be used in the present specification and claims to refer to a chemical substance in a fluid, such as oxygen in air, or glucose in blood, where it is desired to determine the concentration of the chemical substance, such as the oxygen or glucose.

In accordance with one specific embodiment of the invention, the polymeric material may be poly (dimethyl siloxane), commonly known as silicone, for analyzing for the concentration of oxygen in a gas or liquid. By way of background, dimethyl siloxane is a monomer, and the designation "poly (dimethyl siloxane)" is a polymer in which many dimethyl siloxane molecules are linked together, and the parentheses in this expression have a chemical, rather than English language significance. The immobilized fluorophor could be 9,10-diphenyl anthracene. When the fluorophor immobilized in the silicone is excited, it emits output radiation. The presence of oxygen will tend to quench the output radiation of the fluorophor, and will reduce the output radiation. With the polymeric matrix directly exposed to the gas being analyzed, the response time may be on the order of about two or three seconds, as more fully disclosed herein below, as compared with the unreasonably long time period of three minutes or more which has heretofore limited the use of the prior art probes of this general type in practical applications.

In accordance with another specific embodiment of the invention, the concentration of glucose in a fluid, such as blood, may be analyzed by using poly (hydroxyethyl methacrylate), or PHEMA, having a fluorophor and catalytic material physically entrapped therein. The catalytic material may be glucose oxidase, which catalyzes the reaction of glucose and oxygen to produce gluconic acid and hydrogen peroxide, thereby reducing the concentration of oxygen within the matrix when glucose is present; and thereby reducing the quenching action of oxygen which would otherwise take place. Accordingly, with increasing presence of glucose, there is increased fluorescent output. As the radiation output intensity is also dependent on the oxygen concentration in the fluid, this may be concurrently measured using a companion sensor containing the same fluorophor, but not the glucose oxidase, in the polymeric matrix.

A preferred fluorophor for immobilization in the PHEMA is 9,10- diphenyl anthracene. In the second case, as in the first case, the polymeric matrix chemically or physically immobilizes the materials involved in the reactions; and no multiple layers, or enclosing membranes are included in the structure. Such additional layers slow down the detection of the analyte (oxygen and/or glucose), make manufacture more difficult, increase cost, or decrease reliability.

From a somewhat different aspect, the present invention utilizes fluorescent compounds, catalysts and other reagents trapped in polymeric hosts. The fluorescence intensity of the fluorophor is changed by the presence of an analyte in fluid environments surrounding the polymeric host. In the most elementary cases, the analyte reacts directly with the fluorophor via quenching to reduce the fluorescence intensity. More generally, catalysts and other reagents can be incorporated into the polymer host to couple the analyte and fluorophor by any number of chemical reactions. The disclosed materials are formed of a matrix of transparent polymeric material that is permeable to the analyte and that has the fluorophor, catalyst and other essential materials immobilized within the matrix of the polymer host; the resulting composite material is directly exposed to an environment containing the analyte.

The use of a polymeric matrix such as silicone or PHEMA which has good physical strength, as well as the desired transparency and permeability, is useful in avoiding the need for successive layers and/or membranes that have increased the response time of prior proposed devices; and the new composite materials provide for ease of fabrication, reduced cost, and flexibility in design.

Advantages of the new materials and sensor construction include the following:

1) The composite material is a single structure, containing the fluorophor, catalyst, when employed, and possible additional reagents all homogeneously distributed, and not requiring multiple layers, or membranes as are found in prior sensors. The single phase is an advantage because it (a) reduces diffusion path lengths, thereby reducing diffusion time and significantly decreasing the response time of the sensor, and (b) the resulting sensor is much easier and cheaper to manufacture, and (c) tends to be more reliable as a result of its simpler design.

2) Immobilizing the fluorophor in the polymer allows for larger fluorophor concentration. Higher fluorophor concentrations yield larger initial fluorescence intensity, thereby providing a larger dynamic range (i.e., increasing measurable analyte concentration range).

3) The polymer host and reagents can be chosen for increased selectivity of the analyte, and therefore decreased interference by other compounds.

4) The analytes, or compounds to be measured, as well as any products from chemical reactions occurring within the polymer hosts, readily diffuse in and out of the composite material while the fluorophor, and the catalyst, and the reagents, when used, do not leach out of the matrix.

5) The transducer/sensors are reversible, allowing continuous real-time measurement. The oxygen sensor does not consume oxygen, in contrast to prior art oxygen sensors that utilize electrodes and are currently in use for oxygen measurement. The glucose sensor consumes small amounts of both oxygen and glucose, but this does not reduce its effectiveness as a continuous sensor, since in application the amounts of glucose and oxygen which are consumed are not limiting factors in the concentration measurements.

6) The oxygen sensor shows increased stability, increased sensitivity, and greatly decreased reaction time, compared with other optically based oxygen sensors.

7) The glucose transducer has the unusual feature of coupling two chemical reactions within a single solid phase.

8) The composite material does not show memory or hysteresis, and consequently can readily detect increases and decreases in analyte concentration. In other words, these materials form the basis for a reversible sensor.

9) The polymer host, fluorophor, catalysts, and other reagents can be chosen to provide adequate stability for a given application. The resulting composite material will not have the drift found in currently available electrode based chemical sensors.

10) Clinical, non-clinical, and industrial applications can be accommodated by the appropriate choice of constituent elements.

11) The composite matrix is a single solid phase and as such can be readily fabricated into a variety of geometries as required for each application.

Other objects, features and advantages of the invention will become apparent from a consideration of the following detailed description, and from the accompanying drawings.

DETAILED DESCRIPTION

Before describing the drawings in detail, a consideration will be given to certain more general matters relating to the invention.

The present invention in certain aspects relates to composite materials comprised of polymer hosts, fluorescent compounds, catalysts, and other necessary reagents for the detection of particular analytes in environments surrounding said material. Certain of the fundamental chemical and photophysical reactions that occur within the composites may be described by the terms "heterogeneous catalysis" and "fluorescence quenching".

Heterogeneous catalysis occurs as the analyte diffuses from the environment into the composite material, reacts with the catalysts immobilized within the polymer, and the reaction products diffuse out. It is necessary to employ heterogeneous catalysis when the analyte of interest does not directly quench a suitable fluorophor. Any number of chemical reactions can be used to couple the analyte to the fluorophor. The reactions that are catalyzed must consume or produce a compound that does quench fluorescence.

Fluorescence is the absorption and prompt reemission of electomagnetic radiation with change of wavelength, in gases, liquids, and solids. Fluorophors emit radiation outwardly in all directions. Fluorescence quenching results when a molecule in an excited state gives up its energy by a non-radiative transition to a second molecule. The second molecule must lose this energy in a non-radiative manner. Incident radiation of a given range of wavelengths is utilized to raise the immobilized fluorescent component to an excited state. The analyte of interest or suitable compound produced or consumed during heterogeneous catalysis acts to absorb the energy from the fluorescent compound. Thus, the fluorescent compound is reduced to its ground state, light is not emitted and the overall fluorescence intensity of the composite material is decreased. The energy absorbed by the quenching molecule is dissipated non-radiatively to the surrounding polymer host.

Since the catalysts, reagents, and fluorophors are immobilized throughout the polymer, analytes of interest must dissolve into and diffuse through the polymer to reach the active sites. Consequently, diffusion of the analytes within the polymer is an important factor in determining the response time of sensors utilizing the materials. Another factor affecting response time is the geometry of the fluorescent probe.

The device sensitivity and specificity is determined by the reactions occurring within the composite material as well as by the polymer itself. Since the analyte must diffuse into the polymer host, it is important that the polymeric matrix be readily permeable to the analyte. The other constituents of the composite material can be chosen to be specific for a given analyte in a given application.

The disclosed composites are formed of a matrix of polymeric material that is transparent in the wavelengths of interest (e.g. the excitation and emission radiation). The fluorophor, catalyst, and other reagents are immobilized during the polymerization. Physical and/or chemical immobilization can be utilized.

DETAILED DESCRIPTION OF THE DRAWINGS

Figure 1:
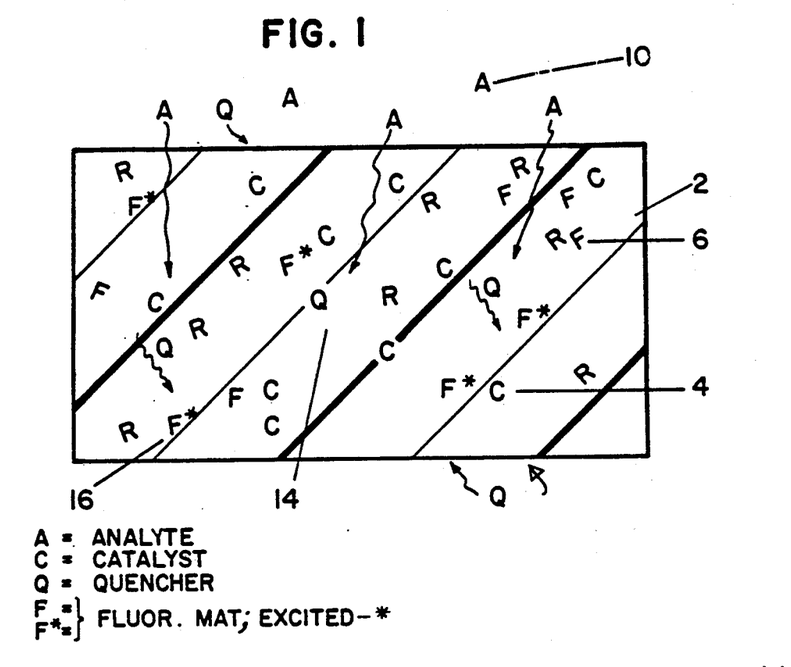
FIG. 1 is a schematic diagram indicating the processes involved in heterogeneous catalysis and photophysical reactions, in a polymeric matrix, illustrating the principles of the invention.

With reference to the drawings, FIG. 1 shows a process illustrating the principles of the invention, and it will be described both generally, and in terms of a specific example.

FIG. 1 represents a polymeric matrix 2 which may be a material such as PHEMA mentioned above, in which a fluorophor 6, also designated by the letter F, is immobilized. When the fluorescent material is in the excited state, it is designated by the symbol $F^*$, as compared with a plain "F", when the fluorophor is not excited by incoming radiation. A catalyst designated by the letter "C" and reference numeral 4 is also immobilized within the polymeric matrix 2. One suitable catalyst for a system involving the detection of glucose concentration is glucose oxidase. The glucose is the analyte, or the substance being analyzed, and it is designated in FIG. 1 by the letter A and the reference numeral 10. The quencher Q is designated by the reference numeral 14, and in this specific case, it would be oxygen.

Now, in FIG. 1 the fluorophor F is irradiated by input radiation of suitable intensity and wavelength and many fluorophor molecules are raised to the excited state $F^*$. The analyte A (for example, glucose) and the quencher Q (for example, oxygen) diffuse into the permeable polymeric matrix 2 and encounter the catalyst C (for example, glucose oxidase) and the excited fluorophor molecules $F^*$. The quencher Q would normally quench the fluorophor output radiation, and would reduce the over-all output radiation proportionally to the quencher (oxygen) concentration. However, the analyte, (glucose) in the presence of the catalyst (glucose oxidase) combines with the quencher (oxygen), to form reaction products (gluconic acid and hydrogen peroxide) thus eliminating the quenching action.

Thus, if the concentration of the quencher (oxygen) is known, the increase in output radiation is a measure of the concentration of the analyte (glucose). In some cases, the quencher may be the analyte, in which case a simpler and more direct relationship is obtained. In addition, in some cases the analyte may react with the catalyst or other reagents to increase the amount of the quencher, thus further reducing the output radiation.

In FIG. 1 the letter "R" designates additional reagents which may be included in the polymeric matrix, to improve probe operation for specific applications. One example of such reagents for medical applications are the fibrinolytic enzymes (e.g. urokinase and streptokinase) which prevent the formation of blood clots on the matrix, that might otherwise impair the permeability of the probe, and its usefulness as a measuring tool.

Figure 2:
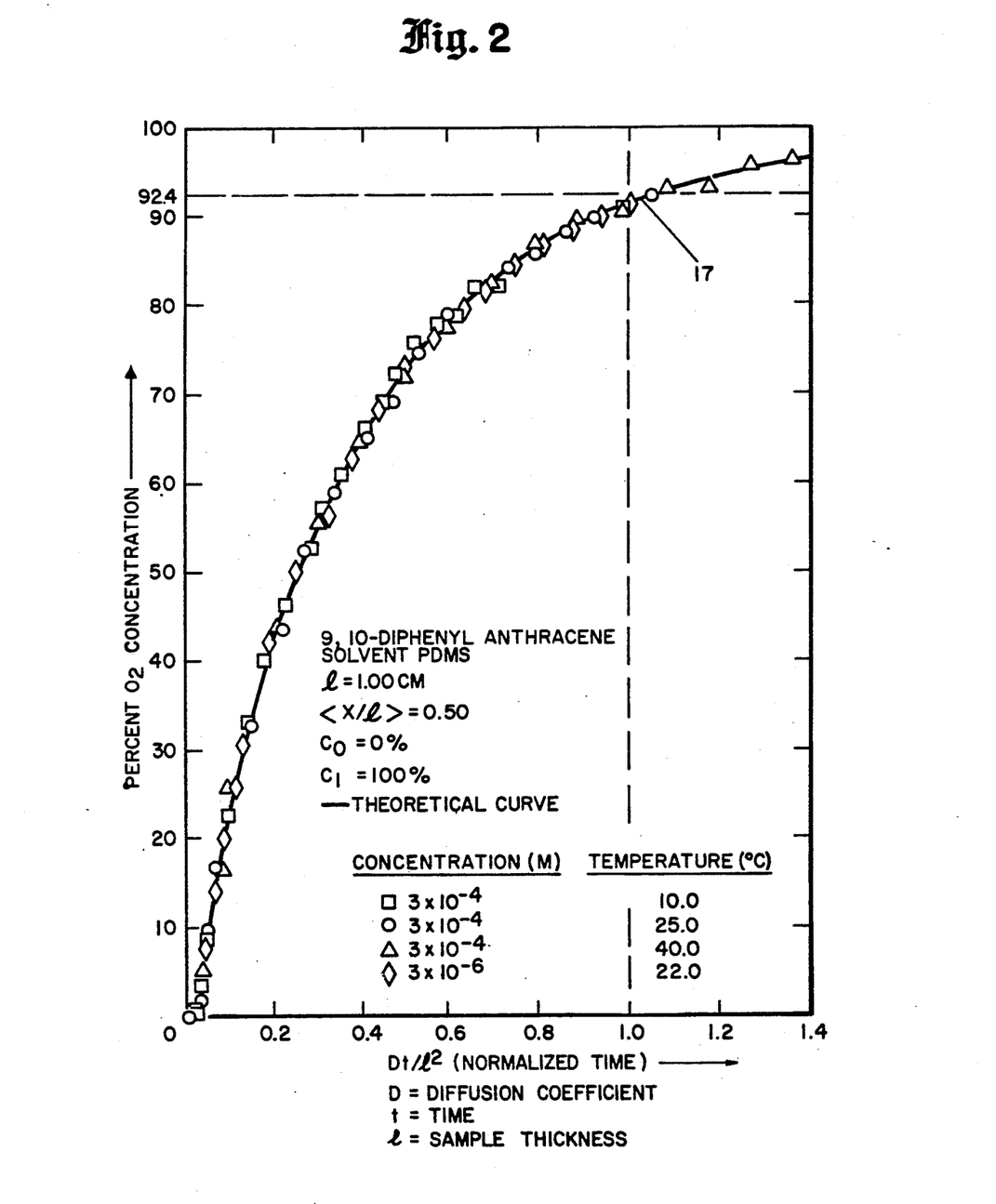
FIG. 2 is a plot of concentration-vs.-normalized time, with the oxygen concentration being plotted as a direct function of time, the diffusion coefficient and as an inverse function of the square of the thickness of the probe.

FIG. 2 shows sample results of several experiments which evaluated the diffusion coefficient, D, of oxygen in PDMS at several temperatures and fluorophor (9,10-diphenyl anthracene) concentrations. For a given sample, FIG. 2 may be viewed as a plot of oxygen concentration vs. normalized time. In the ranges evaluated, D was not a function of initial or final oxygen concentration or of fluorophor concentration. The diffusion coefficient is a function of temperature, obeying an Arrhenius relation. The figure shows how the concentration of oxygen, initially zero within the fluorophor/silicone composite matrix varies with the diffusion coefficient (D), time (t), and thickness "l" in a sample when exposed to an environment that has oxygen present. Shown are sample data for four temperatures and two fluorophor concentrations, as well as the theoretical curve for these experimental conditions. A measure of the device response time at a given temperature is the 92.4% concentration point 17 where $Dt/l^2 = 1.0$. For example, at $T = 37°$ C., $D = 5 \times 10^{-5}$ cm$^2$/s. At this temperature, for a planar sample 100 microns thick, the 92.4% saturation value is achieved in 2 seconds. At 20° C., $D = 3.2 \times 10^{-5}$ cm$^2$/s, and for a 100 microns thick sample, the time to achieve 92.4% saturation is 3.1 seconds. Cylindrical or spherical samples would achieve the 92.4% saturation more rapidly. These relatively short time periods are in contrast to the response time periods for multiple sheath or other similar probe geometries using membranes, of three minutes or more. Thus, by using a geometry in which the permeable transparent polymer matrix as described above is directly exposed to the material being measured, a decrease in response time of one or two orders of magnitude may be achieved, from three minutes or 180 seconds down to about 3 seconds.

Figure 3:
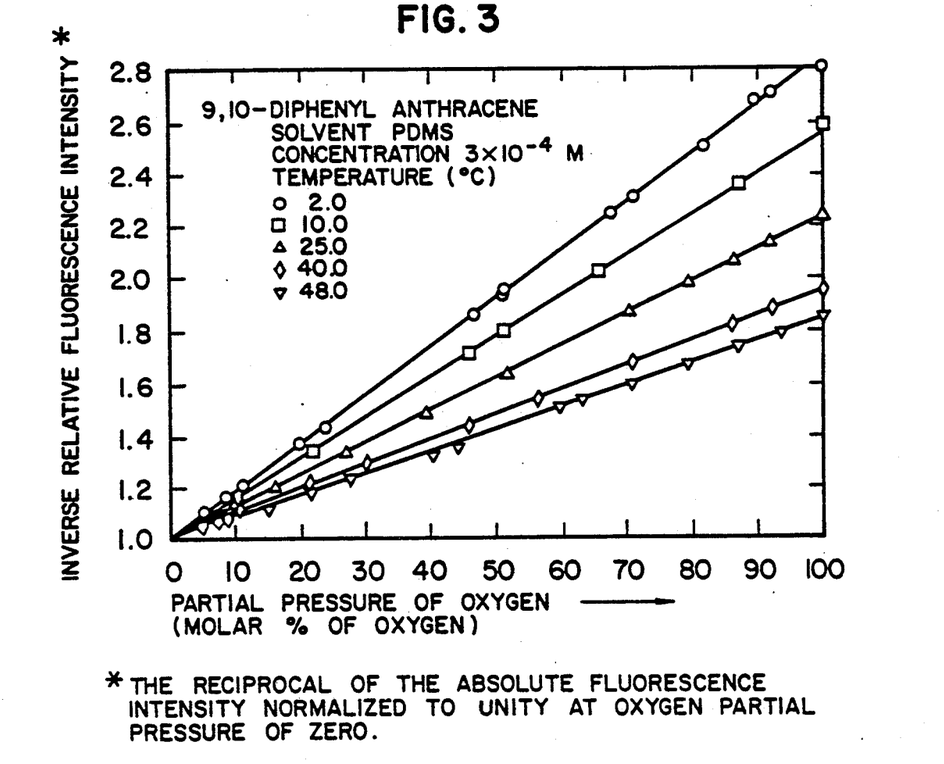
FIG. 3 is a plot showing the linear nature of the inverse relative fluorescence intensity, as a function of the partial pressure of oxygen at several temperatures.

FIG. 3 graphically illustrates experimental results indicating that the relative fluorescence intensity varies linearly with the partial pressure of oxygen surrounding the composite. At a given oxygen partial pressure the concentration of oxygen within the material decreases with increases in temperature. This is demonstrated by the decreasing slopes of the lines with increasing temperature. The slope of a line at a given temperature is representative of the composite matrix sensitivity. Data were taken with increasing and decreasing oxygen concentrations and showed no signs of hysteresis. These experiments were conducted over a three month period, and no fluorophor or polymer degradation was apparent during this period of time.

Figure 4:
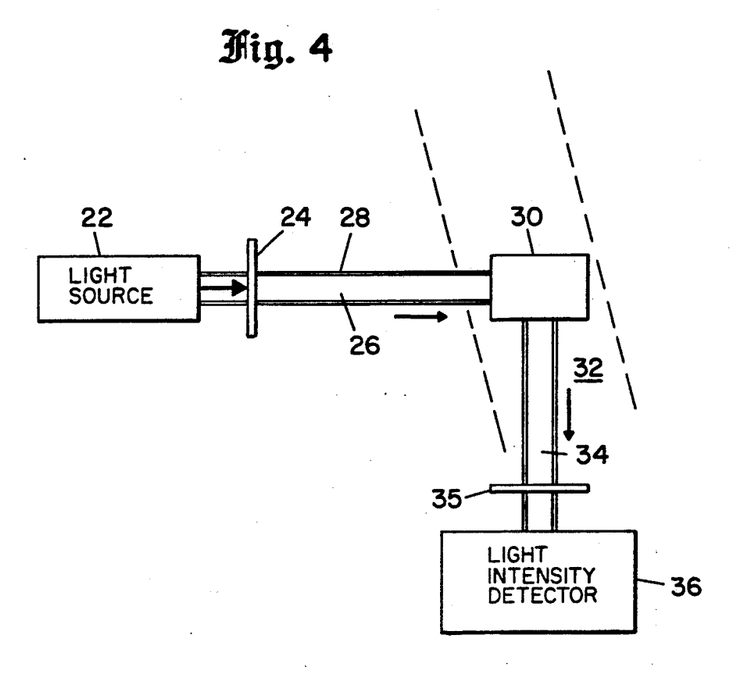
FIGS. 4 and 5 are schematic system diagrams indicating the over-all mode of operation of fluorescent probe systems which are employed in the sensing of analyte concentrations.

FIG. 4 shows an overall system of the type which is involved in the present invention. A light source 22 supplies light through the filter 24 to a fiber optic bundle or light channel 26 which is normally provided with an exterior coating or sheath 28. Light from the fiber optic channel 26 is applied to a fluorescent probe 30.

The fluorescent probe 30 is located within an environment 32 in which it is desired to measure the concentration of oxygen, glucose, or other analyte which will affect the output fluorescence from the fluorescent probe 30. An additional fiber optic element 34 conducts illumination from the probe 30 through the filter 35 to the light intensity detector 36. Although the channel 34 is shown extending at right angles from probe 30, it could of course be at any angle (i.e., 0° to 180°) with respect to input channel 26. A change in output at the light intensity detector 36 indicates that the concentration of the analyte being detected within the environment 32 is changing. Thus, for example, oxygen has the property that it tends to quench or reduce the fluorescent output of many fluorophors. Accordingly, as the concentration of oxygen increases, assuming that the probe 30 is illuminated with a constant level of light from source 22, the amount of radiation transmitted from the probe 30 to the light detector 36 from the fiber optic probe 34 will be significantly reduced. The level of the light detected by the light intensity detector 36 may be calibrated to indicate the concentration of oxygen within the environment 32, to give an accurate indication of the oxygen concentration, as noted above in connection with FIG. 3, for example. Incidentally, the general arrangement as shown in FIG. 4 is known, and the present invention deals primarily with special types of probes which provide very fast reaction time for the system, in the order of one-tenth or one-hundredth, for example, of the time of response of prior proposed arrangements.

Figure 5:
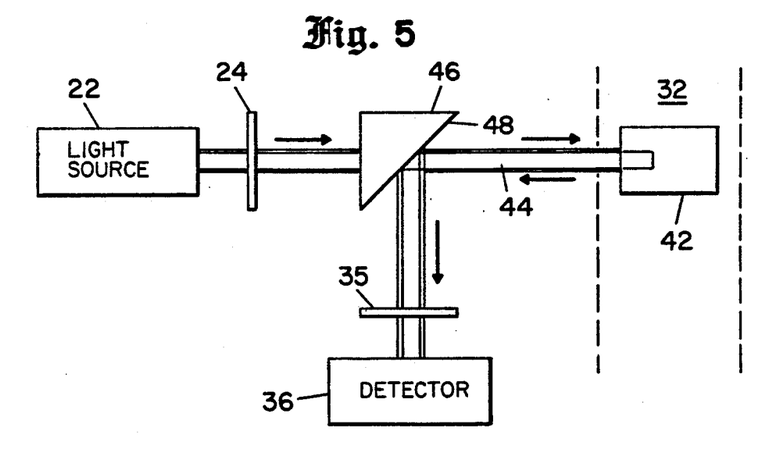

Referring now to FIG. 5 of the drawings, the system is similar to that of FIG. 4, and includes light source 22, filter 24, detector 36 and its associated filter 35, all for determining the concentration of analyte within the environment 32. In the arrangement of FIG. 5, however, the probe 42 both receives illumination and transmits illumination back through the shielded fiber optic channel 44. A light splitter 46 which may include a partially silvered surface 48, permits the direction of illumination from the light source 22 to the fiber optic channel 44, and directs a substantial portion of the light returning toward the left in the fiber optic channel 44 to the detector 36. Incidentally, the output illumination from the fluorophor included in the probe 42, is normally at a different radiation frequency than the excitation frequency supplied by the light source 22. Accordingly, the filter 35 will be suitable for detecting the radiation from the fluorophor in probe 42, and stray radiation of other frequencies will be rejected. In this regard, filter 24 blocks light of the frequencies radiated by the excited fluorophor in probe 42 to increase the sensitivity of the system. The fiber optic probes will normally be arranged and used so that significant levels of stray radiation and illumination of the radiated frequency of the probe will not be picked up at the detectors 36.

Figure 6:
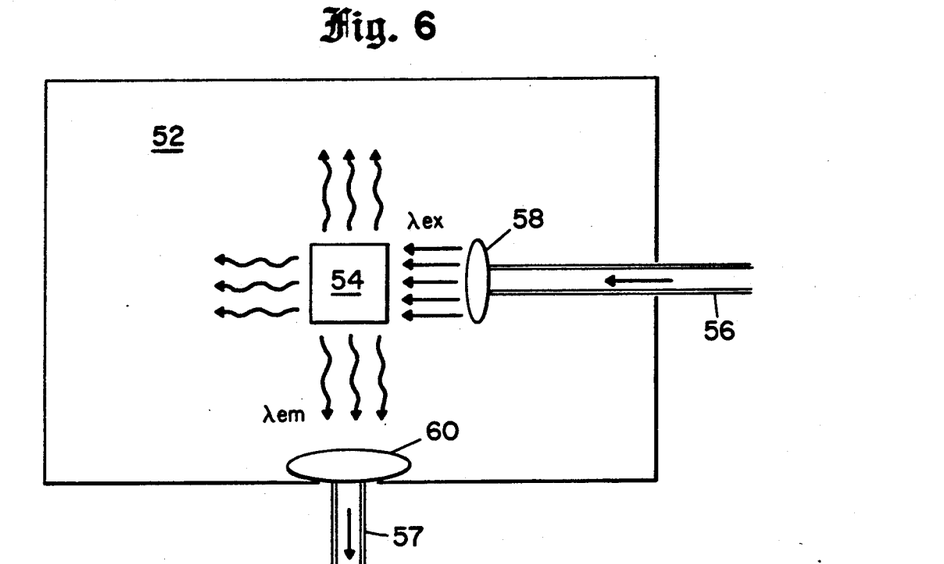
FIG. 6 is a diagram of an experimental arrangement using lenses employed in certain tests relating to the present invention.
Figure 7:
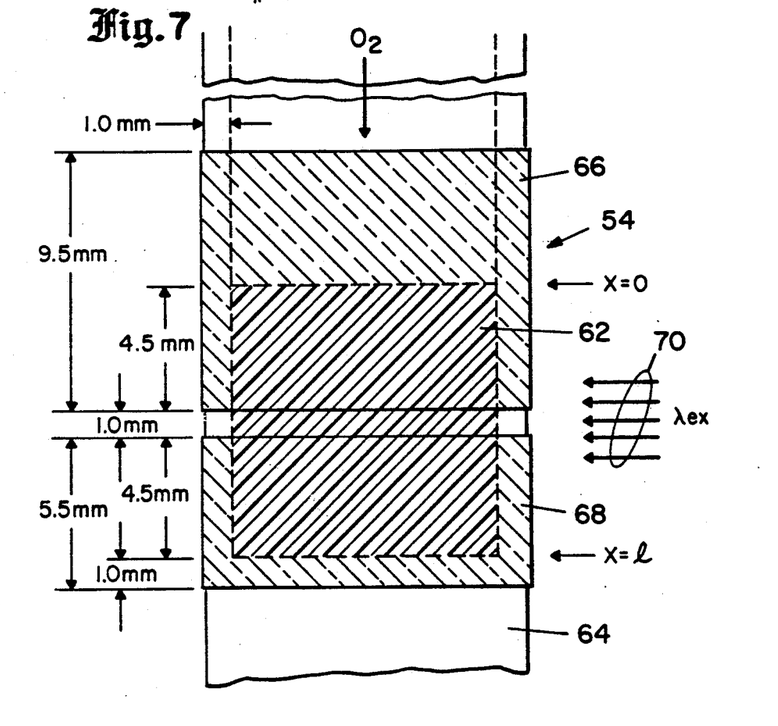
FIG. 7 is an enlargement, showing the sample holding arrangement employed in the test system of FIG. 6.

FIGS. 6 and 7 show schematically, the test arrangements which were employed in the course of testing sample specimens which were prepared. The arrangement of FIG. 6 is also of interest as indicating the use of lenses instead of direct coupling to the fiber optic channels. Thus, for some system applications the fiber optics could even be eliminated. As indicated in FIG. 6, the test arrangements included a light-tight sample compartment 52, enclosing a masked cuvette 54 containing the sample to be tested, and two fiber optic bundles 56 and 57 which extended into the chamber 52. Lenses 58 and 60 were associated with the fiber optic bundles 56 and 57, respectively, in order to maximize coupling between the bundles and the sample within the cuvette 54.

The sample holder for one set of tests is shown in FIG. 7: the cuvette was one centimeter by one centimeter square and had walls which were one millimeter in thickness. A one centimeter cube of silicone 62 containing fluorophor was formed in the bottom of the cuvette, just above the riser block 64. Layers of opaque masking tape 66 and 68 were spaced apart by approximately one millimeter to expose the central portion of the silicone/fluorophor sample. Input radiation of the proper excitation wavelength was supplied to the space between the two masks 66 and 68, as indicated by the arrows 70. Gas containing oxygen was supplied to the upper surface of the sample 62, and the light intensity emitted from the sample 62 was measured, by a detector coupled to the fiber optic bundle 57 shown in FIG. 6, with the over-all system being generally as shown in FIG. 4.

An important feature of the present invention involves the nature of the probe shown at 30 in FIG. 4, 42 in FIG. 5 and at 62 in FIG. 7. It is desirable that the material selected be readily permeable to the analyte which is being detected, that it be transparent at the excitation and emission wavelengths, so that the light may readily penetrate the probe, and the output radiation transmitted therefrom. In most medical applications, it is normally desirable that the probe be biologically compatible. More generally, it is also desirable that the material have sufficient structural integrity so that it may be directly exposed to the material being sensed. In this way, a much shorter response time may be achieved. It has been determined that silicone or PDMS, poly (dimethyl siloxane), forms an excellent host matrix for the fluorescent probe. Another advantage of PDMS is the ability to readily incorporate the fluorophor. Solvents for the various fluorophors, such as benzene, toluene, and xylene, are also soluble in PDMS and evaporate completely from it.

A variety of curing agents are available for silicone, some with amine curing where the agent evaporates. In the experiments employed in connection with the present invention, poly (dimethyl siloxane) gel, R-2602, was used with amine curing agent CAT-05 obtained from McGhan-Nusil. The most commonly used vulcanizing agents for the curing of silicone rubbers are organic peroxides. Used in very low concentrations (in the order of 0.1 to 1.0 weight percentages), the function of the peroxides is to provide free radicals, produced as the peroxides reach their decomposition temperature. The unsaturated bonds capture hydrogen atoms from methyl groups of adjacent linear molecules, causing crosslinkings. In this way the silicone gel becomes a true resilient rubber.

With regard to the fluorophor, any of a number of fluorophors may be employed, and typical aromatic hydrocarbons which may be employed include anthracene; decacyclene; perylene; rubrene; 9-methyl anthracene; 9,10-diphenyl anthracene; 9,10-dichloro anthracene; and tetracene. Each compound possesses an excitation spectrum in the near ultra-violet or low visible wavelength range, and an emission spectrum in the low to mid-visible wavelength range. These excitation and output frequencies are known for each of these compounds, and the filters 24 and 35, for example, in FIGS. 4 and 5, are chosen in order to pass the indicated frequencies.

Reference will now be made to the additional drawings associated with the present patent specification, many of which show specific probe geometries. It is to be emphasized that FIGS. 8 through 21 show various geometries to indicate that virtually any type of geometry may be employed. Thus, the fact that the probe consists of a single composite matrix leads to great flexibility in the final design of the probe. Furthermore, rapid response time is achieved by directly exposing the polymeric matrix containing the fluorophor (and in some cases the catalyst, and/or reagents) to the fluid containing the analyte. Emphasis is placed on the lack of multiple layers or coatings and on the new materials consisting of, for example, a transparent permeable polymeric matrix, including homogeneously distributed fluorophor and catalyst.

Figure 8:
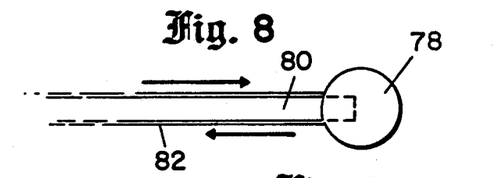
FIG. 8 shows a probe arrangement in which a sphere of transducer material is secured or fixed to the end of a fiber optic element or bundle.

FIG. 8, for example, shows a simple fluorescent probe which includes a sphere of transducer material 78 mounted on a fiber optic element or bundle 80, which is provided with an external coating or sheath 82. Incidentally, in the present drawings, all of the fiber optic elements or bundles have external coatings or sheaths, as is normal with fiber optics. The radiation for exciting the fluorescent material included in the transducer material 78 is sent from left to right down the fiber optic channel 80, and the excited radiation at a different frequency from the element 78 is transmitted back from right to left through the fiber optic channel 80, in a manner similar to the system of FIG. 5 of the drawings.

Figure 9:
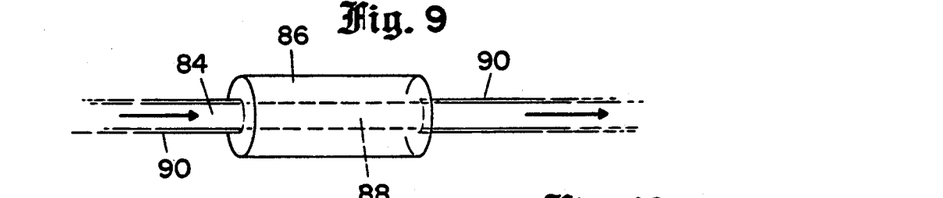
FIG. 9 shows a cylindrical transducer geometry in which the light is transmitted through the fiber to the sensor element from one direction, and output radiation from the fluorophor is transmitted along the fiber optic element in the same direction.

In FIG. 9 of the drawings, a fiber optic channel 84 supplies exciting energy to the fluorescent transducer 86 which is cylindrical in configuration. The transducer 86 is mounted on a section 88 of the fiber optic element or bundle which is free from the external shielding 90 which encloses the fiber optic element or bundle 84, on either side of the transducer member 86. The system with which the arrangement of FIG. 9 would be used, would be similar to that shown in FIG. 4 of the drawings in which the fiber optic elements are only employed for the one-way transmission of radiation, rather than for transmitting light in both directions.

Figure 10:
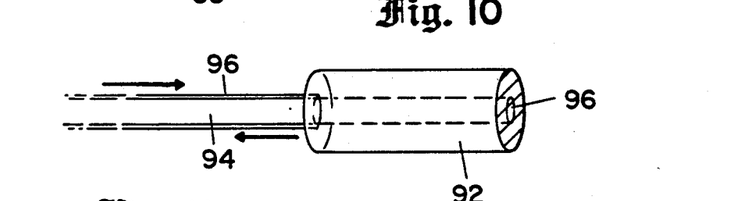
FIG. 10 shows a similar cylindrical geometry, but one wherein the fiber optic element or bundle ends at the remote end of the fluorescent probe, and a single fiber optic bundle both supplies the input radiation in one direction, and conducts the output radiation away from the probe in the opposite direction.

In FIG. 10 of the drawings a transducer assembly is shown including the fluorescent transducer 92 mounted on one end of the fiber optic bundle or element 94. As in the case of prior embodiments, the fiber optic element 94 is provided with a coating or sheath 96 except in the area where it is enclosed by the transducer 92. The radiation excited within the transducer 92 at a different frequency from the incident radiation will be transmitted from right to left through the fiber optic element or bundle 94, in the geometric configuration shown in FIG. 10. If desired, the right-hand end of the fiber optic element and the fluorescent transducer may be coated with reflecting material 96 to increase the reflection of the excited radiation from right to left along the fiber optic channel 94. However, it may be noted that the difference in index of refraction of the fiber optic element or bundle and that of the transducer portion as compared with air, will mean that a substantial portion of the energy is reflected from right to left. Accordingly, the reflecting material, although helpful, is not necessary.

Figure 11:
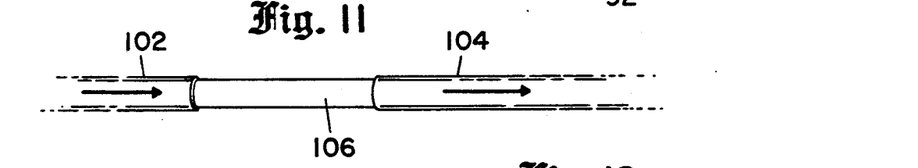
FIG. 11 shows an arrangement in which the transducer material is connected in series with the fiber optics.

In the arrangement of FIG. 11 two sheathed fiber optic channels 102 and 104 are connected in series with a fluorescent transducer 106. With this arrangement as shown in FIG. 11, the incident exciting radiation is supplied from left to right in fiber 102, and is transmitted to the detector at a different frequency on light fiber 104. Incidentally, optical and/or mechanical coupling arrangements, known per se, may be employed in each case at the interface between the fiber optic channel and the probe.

Figure 12:
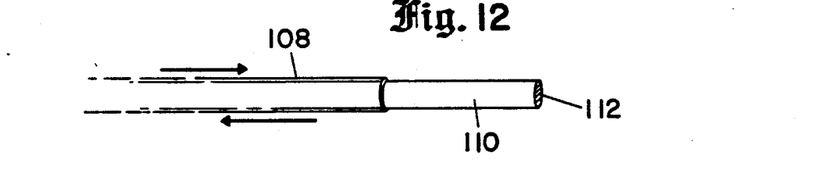
FIG. 12 is a schematic showing of a fluorescent probe, which may be of cylindrical configuration secured to the end of a fiber optic bundle or a fiber optic element, in which the outer end of the transducer may be provided with a reflective coating so that the output radiation is transmitted back along the fiber optic channel.

FIG. 12 is an arrangement similar to that of FIG. 11, wherein the shielded light fiber 108 transmits energy at one frequency to excite the fluorescent material in the transducer 110, but the radiation from the fluorescent material at a different frequency is transmitted back from right to left in the fiber optic element 108. If desired, reflective material 112 may be provided at the outer end of the transducer 110.

In each case, care must be taken to insure that interfering variable stray radiation is either not picked up by the fiber optic element or through the transparent transducer 106 or 110, or that it is filtered out by the filters preceding the detectors. In many cases this will necessarily be the case because the conditions of use and the associated light filters will isolate the transducer output from interfering variable ambient light; however, in some cases additional light shielding may be provided.

Figure 13:
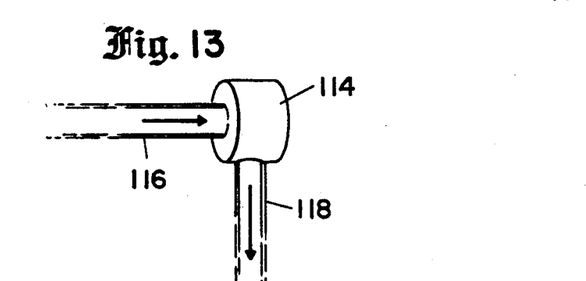
FIG. 13 shows a shortened cylindrical probe with axial input and radial output fiber optics.

In FIG. 13 of the drawings, a cylindrical fluorescent transducer 114 is energized through the sheathed fiber optic element or bundle 116, and the emitted radiation from the transducer element 114 is transmitted through the output fiber optic element 118 to a detector, in a manner similar to that shown in FIG. 4 of the drawings.

Figure 14:
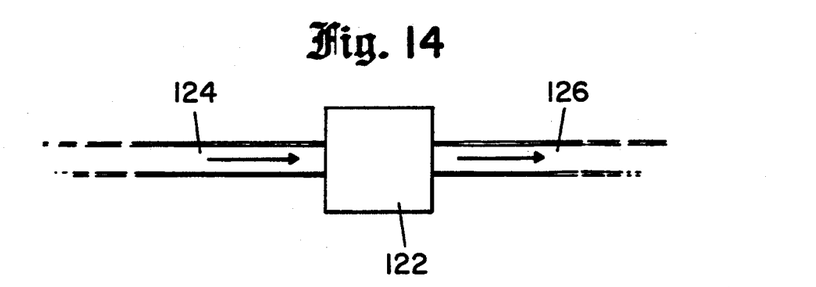
FIG. 14 shows a slightly different embodiment in which the fiber optic channels are coupled to a rectangular block of transducer material.
Figure 15:
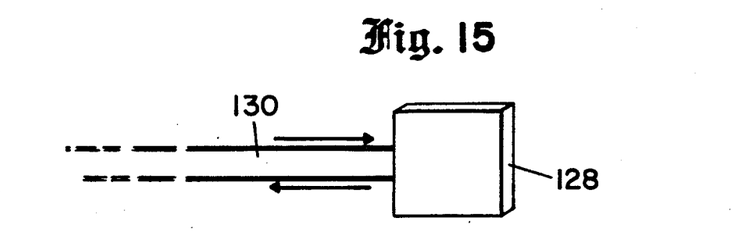
FIG. 15 shows an arrangement similar to that of FIG. 14, but with the remote surface of the transducer being reflective to send light back down the single fiber optic channel.
Figures 16, 17:
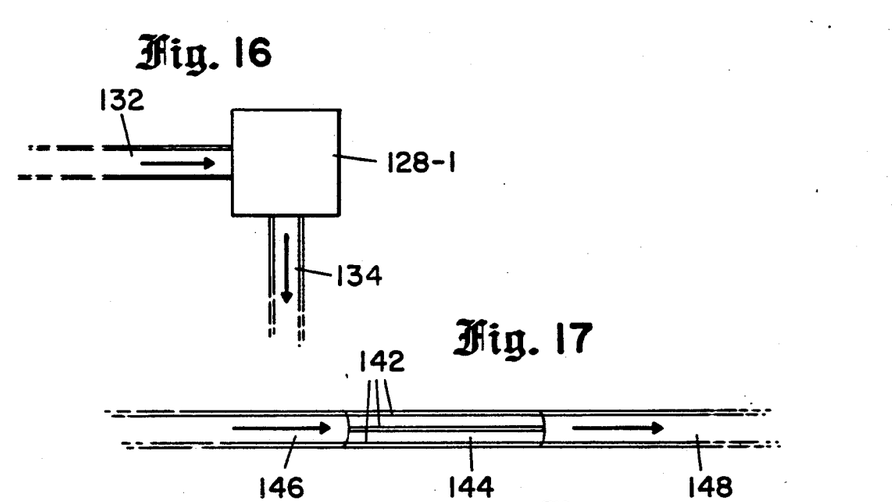
FIG. 16 employs a rectangular transducer with input and output fiber optics at right angles to one another.
FIG. 17 shows a configuration which is similar to the arrangement shown in FIG. 11, but includes exterior mechanical supporting elements interconnecting the two fiber optic channels, without significantly impairing the accessibility of the transducer.

FIGS. 14, 15 and 16 of the drawings are similar to embodiments previously disclosed except for the square geometry of the probe. More specifically, in FIG. 14, a square transducer element 122 is energized on a straight through basis from shielded fiber optic channel 124, and the output radiation generated within the transducer 122 is supplied to the output fiber optic element 126. FIG. 15 shows an alternative embodiment wherein the rectangular fiber optic member 128 has both the input radiation and the output radiation from the fluorescent material transmitted over a single fiber optic channel 130. The arrangement of FIG. 16 is similar to that of FIGS. 14 and 15, but the fluorescent transducer 128-1 is energized from the fiber optic channel 132 and output radiation is transmitted along the channel 134.

It has previously been mentioned that it is desirable to expose the fluorescent transducer material directly to the environment being tested or analyzed, in order to achieve rapid response. In the embodiments of the invention disclosed hereinabove a direct exposure of the element has been shown, and the manner of support of the polymeric material has not been discussed in great detail, as it is not needed in the case of many relatively strong polymeric matrix materials such as PHEMA and PDMS. However, in cases where the polymeric material forming the matrix in which fluorescent material is immobilized, is relatively weak from a structural standpoint, an arrangement such as that shown in FIG. 17 may be employed wherein an enclosing cage or a set of structural supporting elements or rods 142 may be employed to enclose the fluorescent transducer 144, or may be embedded within it. Coated or shielded input and output fiber optic channels 146 and 148 are provided on either side of the fluorescent transducer 144 to provide input excitation and to conduct the variable radiations from the transducer.

Figure 18:
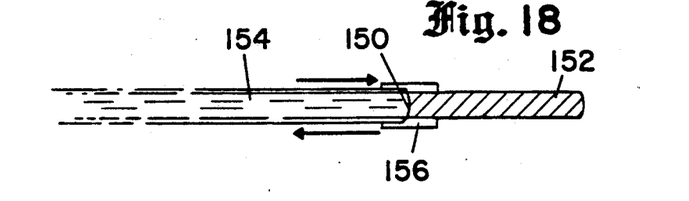
FIG. 18 shows a fiber optic channel with a cylindrical, in-line, transducer having a reflective end, and a support element to more firmly secure the transducer element to the fiber optic channel.

FIG. 18 shows an alternative structural arrangement in which the joint 150 between the transducer 152 and the shielded fiber optic cable 154 is strengthened by a mechanical coupler 156 from the shield of the fiber optic channel to strengthen and at least partially support the transducer 152 so that the bond at the interface 150 would not be the sole support thereof. Support elements as shown in FIG. 17 could be used to provide support to transducer 152 in FIG. 18.

In earlier discussions in the present specification, the use of silicone to physically entrap or immobilize the fluorescent material, and the detection of oxygen as the quenching agent has been discussed. As discussed above, in connection with FIG. 1, a similar but distinctly different fluorescent transducer may be employed to detect levels of glucose which may be present in the bloodstream, or in other fluids. In order to accomplish this purpose, a fluorophor and a catalyst, such as an enzyme, may be immobilized or trapped in a transparent polymer. Thus by way of specific example, the incident radiation that might normally excite the fluorescent material at a relatively high level, is applied to the transducer. Then, in the presence of oxygen, the radiation would be quenched to some extent and the level of output radiation reduced. However, glucose will react with oxygen, in the presence of the enzyme or catalyst, and remove at least some of the oxygen from its previous quenching role. Thus, with increasing glucose present in the fluid, the quenching action is further reduced, and the amount of output radiation is increased.

One example of this type of transducer would involve an enzyme (glucose oxidase) and a fluorophor, such as 9,10-diphenyl anthracene, entrapped within poly (hydroxy-ethyl methacrylate), also known as PHEMA. The fluorescence of the fluorophor is quenched by oxygen. Thus, the fluorophor entrapped within the PHEMA acts as an oxygen sensor. However, glucose and oxygen react in the presence of glucose oxidase to produce gluconic acid and hydrogen peroxide. Accordingly, the local oxygen concentration is diminished in the presence of glucose and the enzyme, and the fluorescence of the fluorophor increases.

A comparison of the fluorescence signals of the fluorophor with and without glucose oxidase in close proximity (i.e., trapped within the same polymer matrix) allows the concentration of glucose to be determined. In this regard, the level of glucose may be determined by the variations in the output fluorescent radiation, with increased radiation indicating that higher percentages of glucose are present, and reacting with the oxygen, to reduce the quenching action of the oxygen on the fluorescent output.

The foregoing and related matters have been discussed above, but are reviewed here, in view of the dual probe shown in FIG. 19 to be discussed below.

Figure 19:
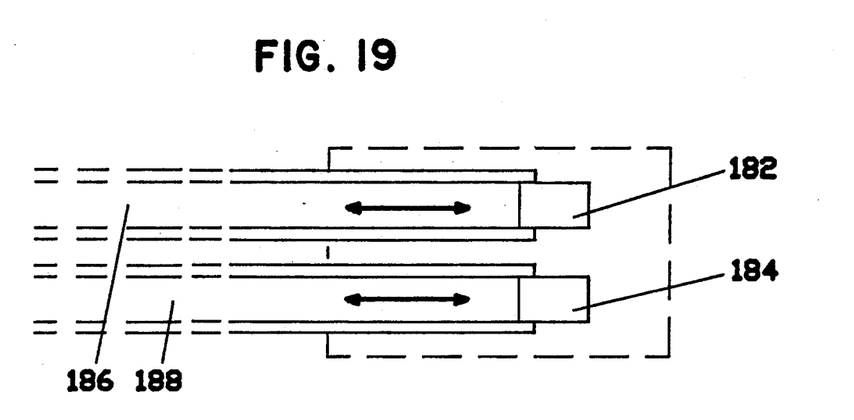
FIG. 19 shows a pair of probes which may be employed together to simultaneously determine glucose and oxygen levels in a fluid, such as blood.

FIG. 19 shows an arrangement in which two separate probes, one for sensing glucose and the other for sensing oxygen, are employed. For convenience, the glucose sensor is designated by reference numeral 182, and the oxygen sensor is designated by the reference numeral 184. In each case, radiation may be supplied to and accepted from the sensors by the coated or shielded fiber optic elements 186, and 188, for the glucose and the oxygen sensors respectively. Separate analyses for the glucose and for the oxygen, are accomplished, in accordance with the arrangements of FIG. 5 of the drawings, using separate detectors. With constant levels of oxygen, the output radiation will vary as a function of glucose concentration; and when both oxygen and glucose concentrations vary, the analysis for glucose must take the varying oxygen concentration into account. It may also be noted that, for the companion sensors of FIG. 19, identical PHEMA matrices and fluorophor concentrations are employed for both sensors, but the glucose oxidase catalyst or enzyme is omitted from the oxygen sensor.

The glucose/oxygen sensor of FIG. 19 may be employed for diabetic persons, to determine the level of glucose present in their bloodstream, and to determine when there is a need for insulin. Such a sensor could be coupled to an insulin pump, thereby creating a closed loop system.

Figure 20:
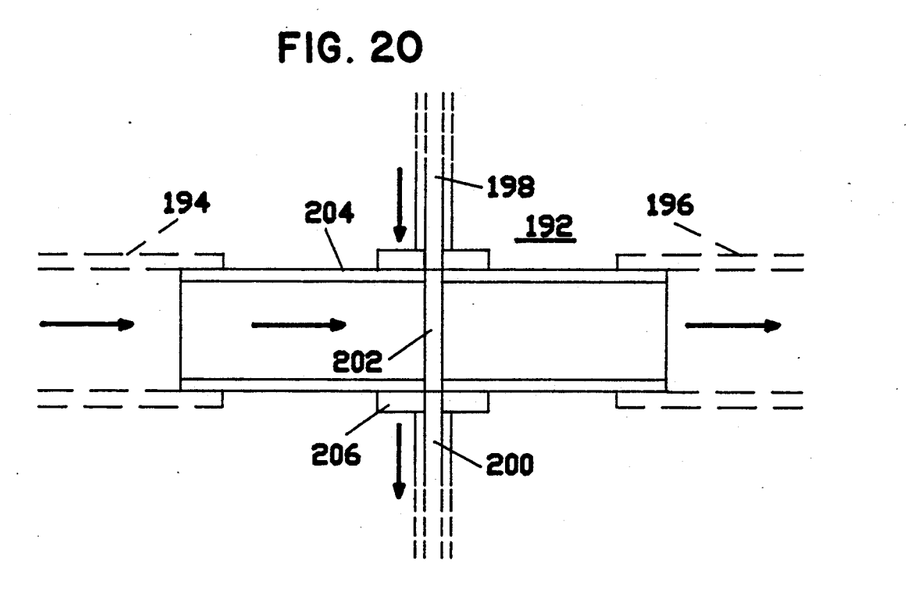
FIG. 20 shows a fluorescent probe mounted across a conduit through which the fluid to be analyzed passes, with fiber optic input and output channels coupled to the fluorescent probe on each side of the conduit.

FIG. 20 shows an embodiment of the invention in which a sensor unit 192 is intended for coupling to input and output conduits 194 and 196. These conduits 194 and 196 may be part of a exhalator system which is analyzing the oxygen content in the exhalations of a patient, with a valve, (not shown) directing air which is being breathed in by the patient in through duct, (not shown), and out through the duct including conduit 194, unit 192 and conduit 196. The unit 192 includes a fiber optic input 198, a fiber optic output channel 200, both of which are coated or sheathed, and a central fluorophor sensing transducer 202 which is mounted in the wall of a conduit 204, with additional connection between the fiber optic channels and the sensor 202 being supported by the ring 206. The sensor 202 may be of cylindrical configuration, if desired, or may be in the form of a very thin rectangular plate, in order to increase the responsiveness of the sensor, and to cut down the time within which the output radiation will reach a stable condition with changes in oxygen content of the air flowing through the conduits.

Figure 21:
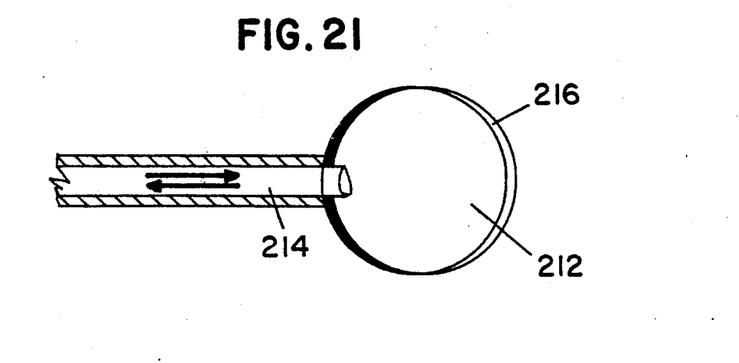
FIG. 21 shows a probe arrangement in which a disc of composite material is secured or fixed in the radial direction to the end of a fiber optic element or bundle.

FIG. 21 shows another alternative probe geometry. In FIG. 21 the probe 212 is disc shaped, and relatively thin. Radiation is applied to the probe 212 and directed back to a detector, through the shielded fiber optic channel 214 in the radial direction. A reflective coating 216 may be applied to the outer cylindrical surface of the probe 212. With the fluorescent probe 212 being formed of any of the matrix and associated materials mentioned in the specification, the geometry, with the thin probe and reflective coating, is chosen to provide rapid response and high output radiation intensity. Typical dimensions for the probe could be a diameter of one centimeter, and a thickness of 200 microns or less.

In the foregoing description, certain specific reactions have been discussed, primarily relative to the use of oxygen as a quenching agent, and focusing on glucose and the catalyst or enzyme glucose oxidase. It is particularly to be noted that other quenching agents, and catalysts may be employed; with the analyte, or material the concentration of which is being studied, being either the quenching substance or a material which alters the concentration of the quencher. It is also noted that the fluorophor and catalyst may be immobilized and held in the polymeric matrix by physical entrapment, or by chemical bonding.

In addition to oxygen, the quenching of radiation from fluorescent compounds can be caused by nitric oxide (NO); metal ions, especially paramagnetic transition-metal ions (e.g., $Fe^{3+}$, $Fe^{2+}$, $Co^{2+}$ and $Mg^{2+}$); heavy atoms such as Zn, Sr, Cd, Ba, and Hg; carbon tetrabromide, $CBr_4$; carbon tetrachloride, $CCl_4$; ethyl iodide; and sulfur dioxide, $SO_2$.

Concerning additional catalyst and analyte combinations, the following may be used:

| Catalyst | Analyte |
| --- | --- |
| Organic Catalysts | |
| L-amino acid oxidase | L-amino acids |
| D-amino acid oxidase | D-amino acids |
| Catalase | Hydrogen peroxide |
| Urate oxidase | Uric acid |
| L-tryphtophan 2,3 dioxygenase | Tryphtophan |
| Urease | Urea |
| Oxalate oxidase | Oxalate |
| Alcohol oxidase | Alcohols, including ethanol |
| Inorganic Catalysts | |
| Vanadium pentoxide | Sulfur dioxide |
| Cuprous oxide | Carbon monoxide |
| Multiple Catalysts (i.e., catalyze sequential reactions) | |
| Xanthine oxide with Superoxide dismutase | Xanthine |

Concerning the immobilization of the fluorophor and/or the catalyst in the polymeric matrix, physical entrapment or chemical bonding may be accomplished. Enzyme immobilization is a rapidly expanding field, with new methods of immobilization being discovered all the time. The methods of immobilization can be quite specific to the catalyst and support system of interest. Possible methods of chemically bonding glucose oxidase include:

1) Glucose oxidase can be vinylated by preincubation with acrylic acid chloride and dichloromethane, and then co-polymerized using N,N-methylenebisacrylamide as the crosslinker.

2) Co-crosslinking with enzymes and gluteraldehyde, and combining the co-crosslinked enzymes in polymers.

3) Chemical modification of the amino acid residue to allow chemical bonding to a polymer.

4) Chemical modification of the carbohydrate moieties and then coupling to amino containing supports.

Similar methods may be able to be used to bind a fluorophor to a polymer support. Fluorescent compounds have readily been combined to proteins in antibody assays. (See, for example, Coons, A. M. and M. M. Kaplin (1950) J. Exp. Med. 91.1.) Once the fluorophors are combined with proteins, the techniques mentioned above can be utilized to bond the fluorophor protein complex directly to the polymer. Furthermore, the organic nature of the fluorophor should enable them to be bound directly to the polymer using some of the above techniques.

Formation of Silicone Matrix

Method for preparing poly (dimethyl siloxane) with 9,10-diphenyl anthracene (9,10-D):

The fabrication of the silicone/fluorophor composite material utilizing PDMS and 9,10-D commences with making a stock solution of the 9,10-D in a solvent, which may for example, be benzene. An accurately measured mass of 9,10-D (e.g. 100 mg) is added to an accurately measured volume of solvent (e.g. 100 ml). A carefully measured volume of the stock solution (e.g. 0.1 ml) is added to a measured volume of the PDMS gel (e.g. 1.0 ml) to make a known concentration of fluorophor in the gel (e.g. 0.1 mg/ml in this case or $3 \times 10^{-4}$ M). The mixture is allowed to sit overnight to allow the solvent (benzene) to evaporate. It could also be placed in a low vacuum (e.g. 100 torr) for a short time, to allow the solvent to volatilize. The curing agent (e.g. CAT 05-an amine curing agent) is added at 0.5 weight percentage and the material is put into a mold or cuvette to cure for 24 hours.

Formation of PHEMA Matrix

Method for preparing the PHEMA with 9,10-diphenyl anthracene and glucose oxidase immobilized in it:

1) A monomer solution consisting of the following components is mixed together:
   9.5 mls of hydroxyethyl methacrylate
   0.5 mls of tetraethylene glycol dimethacrylate
   2.5 mls of ethylene glycol
   0.0025 g 9,10-diphenyl anthracene.

Hydroxy ethyl methacrylate is the monomer. Tetraethylene glycol dimethacrylate is a crosslinker (i.e., crosslinks the chains of PHEMA together). Ethylene glycol stabilizes the entire mixture—without it the aqueous and organic fractions tend to separate. 9,10-diphenyl anthracene is the fluorophor.

2) Two distinct initiator solutions are prepared as follows:

(A) 2 g of ammonium peroxydisulfate are mixed with 5 mls of distilled water.

(B) 0.75 g of sodium metabisulfite is mixed with 5 mls of distilled water.

When the two initiator solutions are combined, they form free radicals, which act to initiate polymerization.

3) An aqueous glucose oxidase solution is prepared by mixing the appropriate amount of glucose oxidase with distilled water. The concentration of the glucose oxidase solutions may range from $1.19 \times 10^{-5}$ g/ml to $4.01 \times 10^{-2}$ g/ml.

4) The monomer solution, both initiator solutions and the glucose oxidase solution are placed in a nitrogen atmosphere for one hour. This causes all of the oxygen to leave the solutions. Oxygen tends to inhibit the free radical polymerization.

5) The monomer solution is mixed with 0.96 mls of each of the other three solutions. The resulting mixture is poured into molds and allowed to polymerize for 12 hours.

6) The polymer samples are removed from the molds and placed in water or buffer solutions.

7) The resulting polymers contain 9,10-diphenyl anthracene and glucose oxidase. They are 37% (by weight) water.

It is to be understood that the foregoing description, and the embodiments shown in the drawings relate to illustrative embodiments of the invention. Various changes may be accomplished without departing from the spirit and scope of the invention. Thus, by way of example but not of limitation, many other fluorophors, catalysts, reagents, and other polymeric materials, both hydrophillic and hydrophobic, may be employed, with it being desirable that the transparent polymeric matrix be directly exposed to the fluid being analyzed, and having a matrix which chemically or physically immobilizes the fluorophor, catalyst and/or the reagent. It may be noted that the supports for the transducer material as shown in FIGS. 17 and 18 may be either metallic or plastic. Accordingly, the present invention is not limited to the embodiments precisely as shown or described here and above.

What is claimed is:

1. A system for rapidly detecting the concentration of an analyte in a fluid comprising:

a fluorescent probe;

means for exposing said probe to a fluid to be analyzed;

means for directing exciting illumination into said fluorescent probe;

means for detecting radiation originating in said fluorescent probe and changes in the radiation with variations in the concentration of said analyte;

said probe being formed of a transparent polymeric matrix having a fluorophor immobilized within the body of said polymeric material, said polymeric material being permeable to the substance being analyzed;

said fluorophor being 9,10 diphenyl anthracene;

means for mounting said probe with said polymeric matrix directly exposed to the fluid to be analyzed, whereby the response time of said system is minimized; and ease of manufacturing and design flexibility are increased;

said polymeric matrix being substantially pure poly (dimethyl siloxane); and fibrinolytic enzymes included in said polymeric matrix, whereby the formation of blood clots is inhibited.

* * * * *